(12) United States Patent
Greenberg et al.

(10) Patent No.: US 8,131,375 B2
(45) Date of Patent: Mar. 6, 2012

(54) TRANS-RETINAL FLEXIBLE CIRCUIT ELECTRODE ARRAY

(75) Inventors: Robert J. Greenberg, Los Angeles, CA (US); Mark S. Humayun, Glendale, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 818 days.

(21) Appl. No.: 11/521,281

(22) Filed: Sep. 13, 2006

(65) Prior Publication Data

US 2007/0049987 A1    Mar. 1, 2007

Related U.S. Application Data

(63) Continuation-in-part of application No. 10/393,887, filed on Mar. 21, 2003, now Pat. No. 7,483,750, and a continuation-in-part of application No. 11/413,689, filed on Apr. 28, 2006, which is a continuation-in-part of application No. 11/207,644, filed on Aug. 19, 2005, now Pat. No. 8,014,878.

(60) Provisional application No. 60/718,779, filed on Sep. 19, 2005, provisional application No. 60/676,008, filed on Apr. 28, 2005.

(51) Int. Cl.
*A61N 1/36* (2006.01)
(52) U.S. Cl. ........................................................ 607/54
(58) Field of Classification Search .............. 607/53–54, 607/116, 152; 623/6.63
See application file for complete search history.

(56) References Cited

U.S. PATENT DOCUMENTS

| | | | |
|---|---|---|---|
| 5,016,633 A * | 5/1991 | Chow | 607/53 |
| 5,109,844 A | 5/1992 | de Juan, Jr. et al. | |
| 5,575,813 A | 11/1996 | Edell et al. | |
| 5,935,155 A | 8/1999 | Humayun et al. | |
| 5,944,747 A | 8/1999 | Greenberg et al. | |
| 6,374,143 B1 | 4/2002 | Berrang et al. | |
| 6,400,989 B1 | 6/2002 | Eckmiller | |
| 6,458,157 B1 | 10/2002 | Suaning | |
| 6,516,228 B1 | 2/2003 | Berrang et al. | |
| 6,843,870 B1 | 1/2005 | Bluger | |
| 7,107,104 B2 * | 9/2006 | Keravel et al. | 607/116 |
| 7,146,221 B2 * | 12/2006 | Krulevitch et al. | 607/116 |
| 2001/0037061 A1 | 11/2001 | Eckmiller et al. | |

(Continued)

OTHER PUBLICATIONS

Shihab A. Shamma-Donoghue, et al, Thin-Film Multielectrode Arrays for a Cochlear Prosthesis. IEEE Trans. Elec. Dev., vol. ED-29, No. 1, Jan. 1982, 9 pages.

*Primary Examiner* — Scott Getzow
*Assistant Examiner* — Amanda Patton
(74) *Attorney, Agent, or Firm* — Scott B. Dunbar; Alessandro Steinfl; Daniel Ueno

(57) ABSTRACT

Applicant has proposed a combination of the subretinal and epiretinal methods by placing the electronics external to the eye, entering the eye through the pars plana and the piercing the retina (retinotomy) from inside the eye to stimulate subreintally.

The present invention is an improved electrode array for subretinal stimulation. A hard polymer such as polyimide is biocompatible and strong for supporting an electrode array and supporting traces in a thin flex circuit array. In the present invention applicant takes advantage of the sharp nature of thin polyimide making a point on the end of the electrode array. This allows the flexible circuit electrode array to be both electrode array and surgical tool to cut the retinal and slide the array under the retina in a single action.

14 Claims, 6 Drawing Sheets

U.S. PATENT DOCUMENTS

| | | |
|---|---|---|
| 2002/0091421 A1 | 7/2002 | Greenberg et al. |
| 2002/0111658 A1* | 8/2002 | Greenberg et al. ........... 607/116 |
| 2002/0193845 A1 | 12/2002 | Greenberg et al. |
| 2002/0198573 A1 | 12/2002 | Nisch et al. |
| 2003/0036790 A1 | 2/2003 | Corbett, III et al. |
| 2003/0093066 A1 | 5/2003 | Peyman |
| 2003/0158588 A1 | 8/2003 | Rizzo et al. |
| 2003/0233134 A1* | 12/2003 | Greenberg et al. ............. 607/36 |
| 2004/0186533 A1 | 9/2004 | Greenberg et al. |
| 2005/0196421 A1 | 9/2005 | Hunter et al. |

* cited by examiner

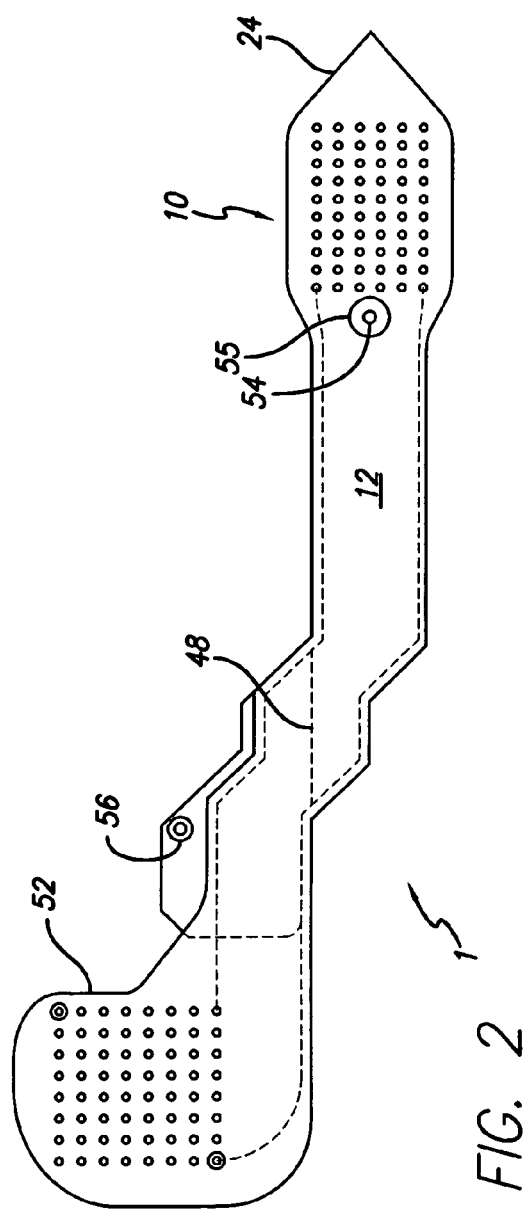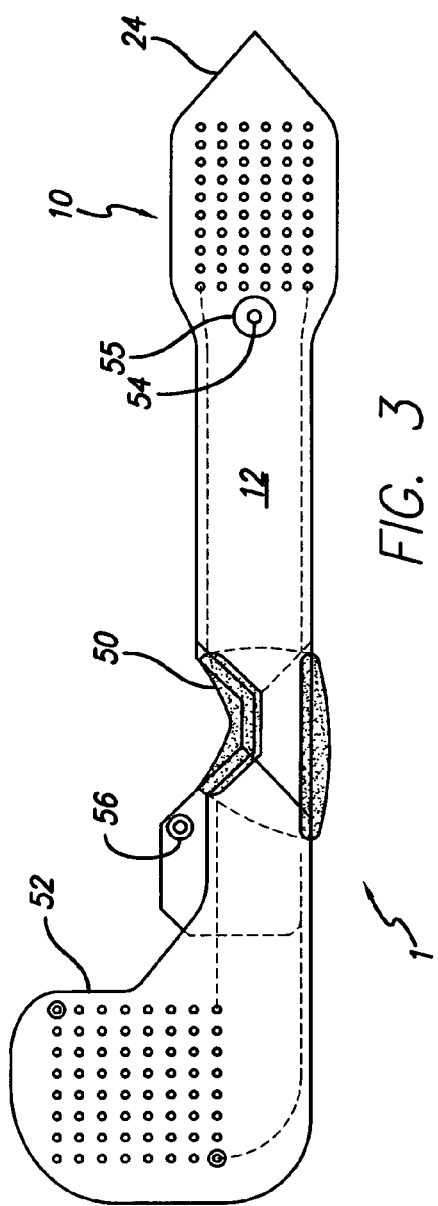
FIG. 2
FIG. 3

TRANS-RETINAL FLEXIBLE CIRCUIT ELECTRODE ARRAY

CROSS-REFERENCE TO RELATED APPLICATIONS

This claims the benefit of U.S. Provisional Application No. 60/718,779, "Transretinal Flexible Circuit Electrode Array", filed Sep. 19, 2005, the disclosures of all are incorporated herein by reference.

This application is a Continuation-In-Part of U.S. application Ser. No. 10/393,887, "Transretinal Implant and Method of Manufacture", filed Mar. 21, 2003 now U.S. Pat. No. 7,483,750, the disclosure of which is incorporated herein by reference.

This application is a Continuation-In-Part of U.S. application Ser. No. 11/413,689, "Flexible circuit electrode array", filed Apr. 28, 2006, which is a Continuation-In-Part of U.S. application Ser. No. 11/207,644, "Flexible circuit electrode array", filed Aug. 19, 2005 now U.S. Pat. No. 8,014,878 which claims the benefit of U.S. Provisional Application No. 60/676,008, "Thin Film Electrode Array", filed Apr. 28, 2005, the disclosures of all are incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved electrode array for subretinal stimulation.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prostheses for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatus to aid the visually impaired. Specifically, great effort has been expended in the area of intraocular retinal prosthetic devices in an effort to restore vision in cases where blindness is caused by photoreceptor degenerative retinal diseases; such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, control the electronic field distribution and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY OF THE INVENTION

Applicant has proposed a combination of the subretinal and epiretinal methods by placing the electronics external to the eye, entering the eye through the pars plana and then piercing the retina (retinotomy) from inside the eye to stimulate subretinally.

The present invention is an improved electrode array for subretinal stimulation. A hard polymer such as polyimide is biocompatible and strong for supporting an electrode array and supporting traces in a thin flex circuit array. The applicants describe the disadvantage of material such as polyimide is that when made thin, it can cut delicate retina tissue. The application further describes methods of protecting the retina. In the present invention applicant takes advantage of the sharp nature of thin polyimide making a point on the end of the electrode array. This allows the flexible circuit electrode array to be both electrode array and surgical tool to cut the retinal and slide the array under the retina in a single action.

The novel features of the invention are set forth with particularity in the appended claims. The invention will be best understood from the following description when read in conjunction with the accompanying drawings.

BRIEF DESCRIPTION OF THE DRAWINGS

FIG. 2 depicts the flexible circuit array before it is folded and attached to the implanted portion.

FIG. 3 depicts the flexible circuit array folded.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
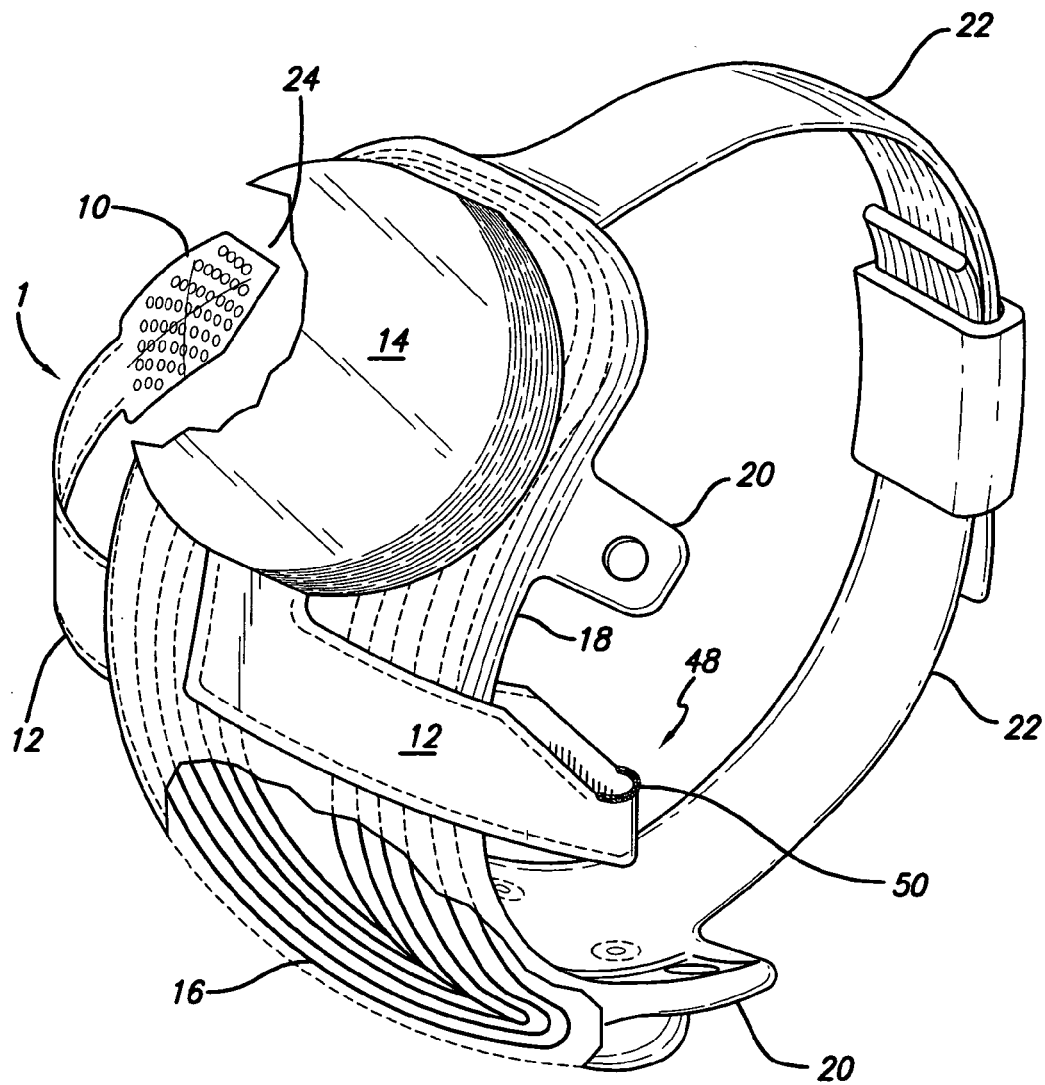
FIG. 1 is a perspective view of the implanted portion of the preferred retinal prosthesis.

FIG. 1 shows a perspective view of the implanted portion of the preferred retinal prosthesis. A flexible circuit 1 includes a flexible circuit electrode array 10. The flexible circuit electrode array 10 is electrically coupled by a flexible circuit cable 12, which pierces first the sclera, then the retina and is electrically coupled to an electronics package 14, external to the sclera. The flexible circuit 1 further forms a point 24 at its end, beyond the flexible circuit electrode array 10. While the point 24 aids in passing the flexible circuit 1 through the sclerotomy, it is particularly useful for passing the flexible circuit 1 through the retina. While the sclera is relatively tough and requires a sclerotomy, the retina is very soft. The point 24 can cut the retina (retinotomy) as in is inserted. This minimizes the size of the retinotomy, reduces the chances of hemorrhage or retina detachment, and simplifies the implant surgery.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

The flexible circuit 1 is a made by the following process. First, a layer of polymer (such as polyimide, fluoro-polymers, silicone or other polymers) is applied to a support substrate (not part of the array) such as glass. Layers may be applied by spinning, meniscus coating, casting, sputtering or other physical or chemical vapor deposition, or similar process. Subsequently, a metal layer is applied to the polymer. The metal is patterned by photolithographic process. Preferably, a photo-resist is applied and patterned by photolithography followed by a wet etch of the unprotected metal. Alternatively, the metal can be patterned by lift-off technique, laser ablation or direct write techniques.

It is advantageous to make this metal thicker at the electrode and bond pad to improve electrical continuity. This can be accomplished through any of the above methods or electroplating. Then, the top layer of polymer is applied over the metal. Openings in the top layer for electrical contact to the electronics package 14 and the electrodes may be accomplished by laser ablation or reactive ion etching (RIE) or photolithograph and wet etch. Making the electrode openings in the top layer smaller than the electrodes promotes adhesion by avoiding delaminating around the electrode edges.

The implanted portion of the retinal prosthesis includes the additional feature of a gentle twist or fold 48 in the flexible circuit cable 12, where the flexible circuit cable 12 passes through the sclera (sclerotomy). The twist may be a simple sharp twist, or fold 48; or it may be a longer twist, forming a tube. While the tube is rounder, it reduces the flexibility of the flexible circuit. A simple fold 48 reduces the width of the flexible circuit with only minimal impact on flexibility.

Further, silicone or other pliable substance may be used to fill the center of the tube or fold 48 formed by the twisted flexible circuit cable 12. Further it is advantageous to provide a sleeve or coating 50 that promotes healing of the sclerotomy. Polymers, such as polyimide, which may be used to form the flexible circuit cable 12 and flexible circuit electrode array 10, are generally very smooth and do not promote a good bond between the flexible circuit cable 12 and scleral tissue. A sleeve or coating of polyester, collagen, silicone, Gore-tex or similar material would bond with scleral tissue and promote healing. In particular, a porous material will allow scleral tissue to grow into the pores promoting a good bond.

It is also advantageous to create a reverse curve or service loop in the flexible circuit cable 12 of the flexible circuit electrode array to gently lift the flexible circuit cable 12 off the retina and curve it away from the retina, before it pierces the sclera at a sclerotomy. This service loop reduces the likelihood of any stress exerted extraocularly from being transmitted to the electrode region and retina. It also provides for accommodation of a range of eye sizes.

With existing technology, it is necessary to place the implanted control electronics outside of the sclera, while a retinal flexible circuit electrode array must be inside the sclera in order to contact the retina. The sclera is cut through at the pars plana, forming a sclerotomy, and the flexible circuit passed through the sclerotomy. A flexible circuit is thin but wide. The more electrode wires, the wider the flexible circuit must be. It may be difficult to seal a sclerotomy over a flexible circuit wide enough to support enough wires for a high resolution array. A narrow sclerotomy is preferable.

FIG. 2 shows the flexible circuit electrode array prior to folding and attaching the array to the electronics package 14. At one end of the flexible circuit cable 12 is an interconnection pad 52 for connection to the electronics package 14. At the other end of the flexible circuit cable 12 is the flexible circuit electrode array 10. Further, a point 24 is provided at the end of the flexible circuit electrode array 10. The flexible circuit cable 12 is formed in a dog leg pattern so than when it is folded at fold 48 it effectively forms a straight flexible circuit cable 12 with a narrower portion at the fold 48 for passing through the sclerotomy.

FIG. 3 shows the flexible circuit electrode array after the flexible circuit cable 12 is folded at the fold 48 to form a narrowed section. The flexible circuit cable 12 may include a twist or tube shape as well. With a retinal prosthesis as shown in FIG. 1, the bond pad 52 for connection to the electronics package 14 and the flexible circuit electrode array 10 are on opposite side of the flexible circuit. This requires patterning, in some manner, both the base polymer layer and the top polymer layer. By folding the flexible circuit cable 12 of the flexible circuit electrode array 10, the openings for the bond pad 52 and the electrodes are on the top polymer layer and only the top polymer layer needs to be patterned. Further, a point 24 is provided at the end of the flexible circuit electrode array 10. The point 24 shown in FIGS. 2 and 3 is formed throughout the hole thickness of the array. The array may contain at least one bottom layer containing at least one polymer, copolymer, blockcopolymer or mixtures thereof and at least one top layer containing at least one polymer, copolymer, blockcopolymer or mixtures thereof. The polymer may be polyimide, silicone, PEEK polymer, a repeat unit that comprises of oxy-1,4-phenylenoeoxy-1,4-phenylene-carbonyl-1,4-phenylene, parylene or mixtures thereof.

Also, since the narrowed portion of the flexible circuit cable 12 pierces the sclera, shoulders formed by opposite ends of the narrowed portion help prevent the flexible circuit cable 12 from moving through the sclera. It may be further advantageous to add ribs or bumps of silicone or similar material to the shoulders to further prevent the flexible circuit cable 12 from moving through the sclera.

Further it is advantageous to provide a suture tab 56 in the flexible circuit body near the electronics package to prevent any movement in the electronics package from being transmitted to the flexible circuit electrode array 10. Alternatively, a segment of the flexible circuit cable 12 can be reinforced to permit it to be secured directly with a suture. The retina tack (not shown) is placed through an attachment point 54 to hold the flexible circuit electrode array 10 to the retina. A stress relief 55 can be made of a softer polymer than the flexible circuit 1.

Figure 4:
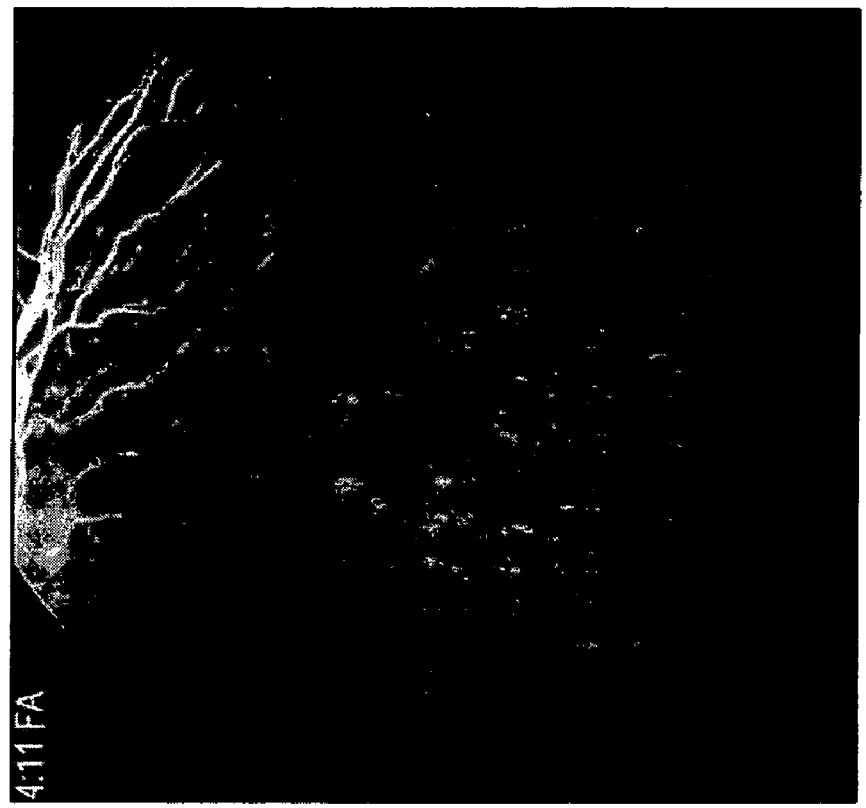
FIG. 4 is a fundus photo and flourescein angiogram after 3 month of the preferred trans-retinal implant in a rabbit.
Figure 4:
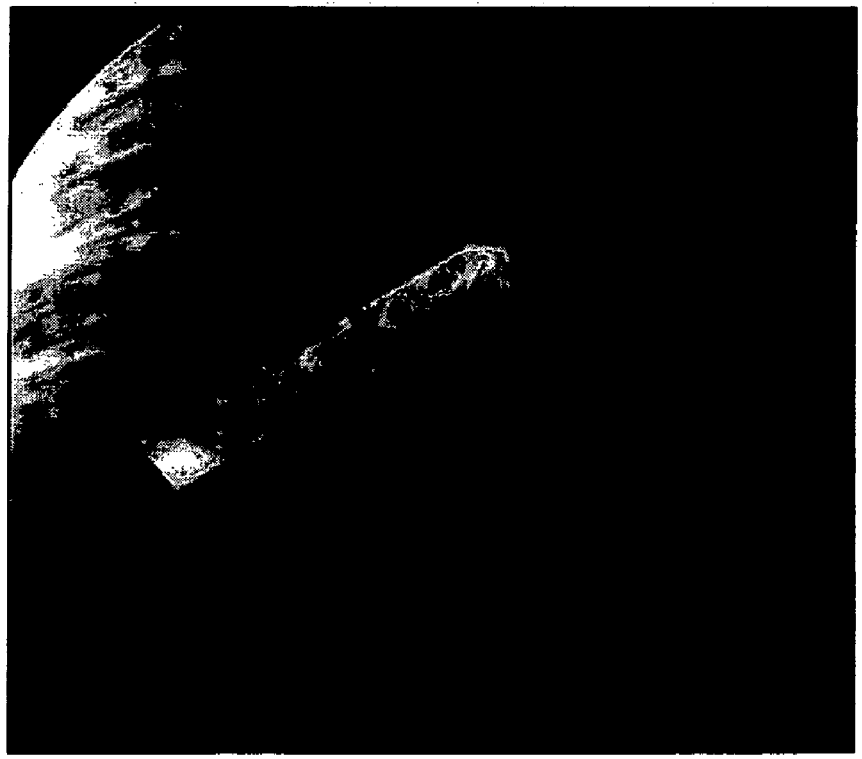

FIG. 4 shows a fundus photo and flourescein angiogram after 3 month of the preferred flexible circuit 1 implant in a rabbit. It is shown that the point 24 of the flexible circuit 1 cuts the retina as it is inserted. 15 rabbits were chronically implanted for over three months each with polyimide flexible circuit 1 which were from 0.3 mm to 0.7 mm, preferably about 0.5 mm wide and from 3.5 mm to 4.5 mm, preferably about 4 mm long using the preferred trans-retinal surgical approach which included laser treatment around the retinotomy site. The flexible circuit 1 were inserted under the retina and left with a portion of the flexible circuit cable 12 sticking out into the vitreous. In an actual device, according the present invention, the flex circuit cable 12 of FIG. 4 would be attached to an electronics package 14 as described above.

Figure 5:
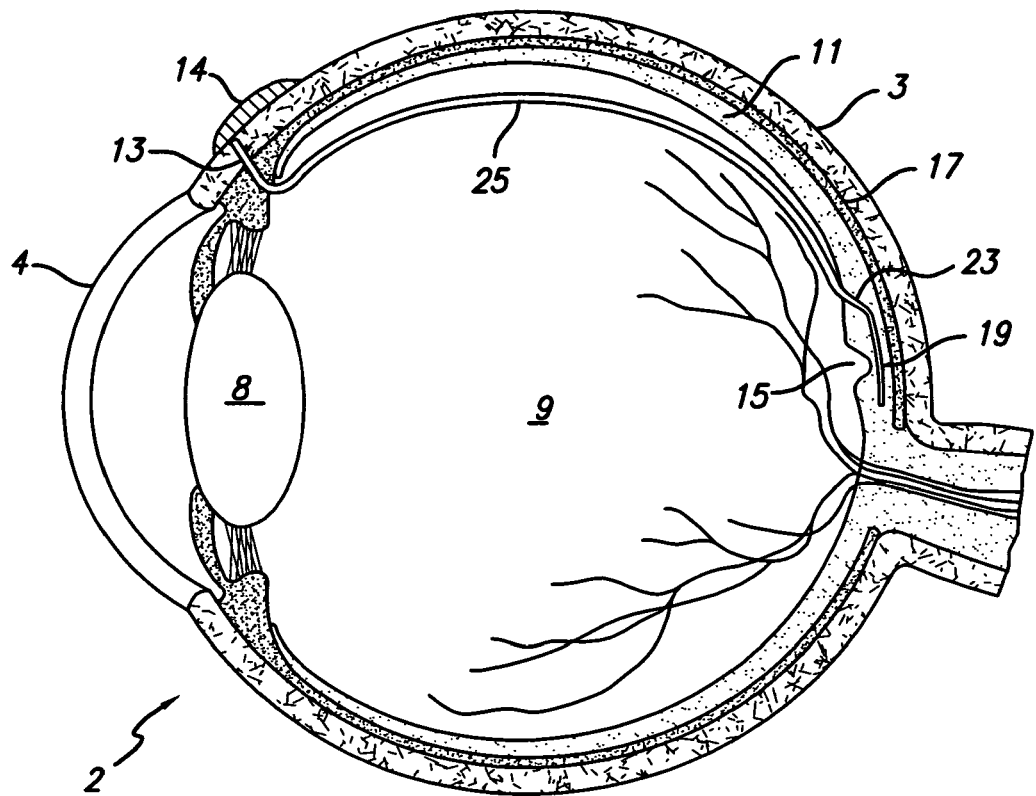
FIG. 5 illustrates a cross-sectional view of an eye showing the placement of the retinal implant and associated electronics.

FIG. 5 provides a cross-sectional view of a preferred embodiment of the eye 2 with a retinal implant 19 placed subretinally. The current invention involves the use of an electronic device, a retinal implant 19 that is capable of mimicking the signals that would be produced by a normal inner retinal photoreceptor layer. When the device is implanted subretinally between the inner and outer retinal layers, it will stimulate the inner layer to provide significantly useful formed vision to a patient who's eye no longer reacts to normal incident light on the retina 20. Patient's having a variety of retinal diseases that cause vision loss or blindness by destruction of the vascular layers of the eye, including the choroid, choriocapillaris, and the outer retinal layers, including Bruch's membrane and retinal pigment epithelium. Loss of these layers is followed by degeneration of the outer portion of the inner retina, beginning with the photoreceptor layer. The inner retina, composed of the outer nuclear, outer plexiform, inner nuclear, inner plexiform, ganglion cell and nerve fiber layers, may remain functional. Functioning of the inner retina allows electrical stimulation of this structure to produce sensations of light or even vision.

The biocompatible retinal implant 19 is attached by an electrically conductive cable or lead wire 25 that is also biocompatible, to a control electronics 14 package that contains suitable electronics to generate an electrical signal that is transmitted along a lead wire 25 to the retinal implant, which stimulates the retina 11. The lead wire 25 passes transretinally through retinal incision 13 and enters the vitreous cavity 9. The lead wire 25 then passes transsclera at sclera incision 13 that passes through the sclera at a location near the front of the eye where there is no retina 11.

The eye 2 has a cornea 4, lens 8, and vitreous cavity 9 through which light normally passes, prior to striking the retina 11 and causing vision. The eye 2 has an outer layer, called the sclera 6, and a nutrient rich layer, called the choroid 18, that is located between the retina 11 and the sclera 6.

In a preferred embodiment, the retinal implant 20 is located subretinally near the fovea 15 to provide good electrical contact between the retinal implant 19 and the retina 11. The lead wire 25, which is attached to the retinal implant 19, proceeds transretinally through retina 11 via retinal incision 23. Passing the lead wire into the vitreous cavity 9 via the retinal incision 23 avoids disrupting the delicate choroid 17, and thereby avoids interfering with the supply of nutrients to the retina 11. The lead wire 25 passes through the vitreous cavity to a point near the front of the eye 2 where it traverses transsclera via an incision 13 through the sclera 6 at a point where the retina 11 and choroid 17 are not present, thereby further avoiding disruption to the blood supply, oxygen, and nutrients that are needed to sustain the retina 11. While the choroid 17 does extend to this region of the eye near the lens 8, called the pars plana, choroid 17 bleeding will not damage the retina 11, and is far less likely to spread to the central retina 11, called the macula, which is the area of most sensitive vision, while choroid 17 bleeding under the retina 11 can track along the retina 11 and end up damaging the macular region near the fovea 19 of the retina 11.

The control electronics 14 are located outside the eye 2 and are attached to lead wire 25. The control electronics 14 are preferably attached to the sclera 6 by sutures. In alternative embodiments, the control electronics 14 are located distant from the eye 2.

Figure 6:
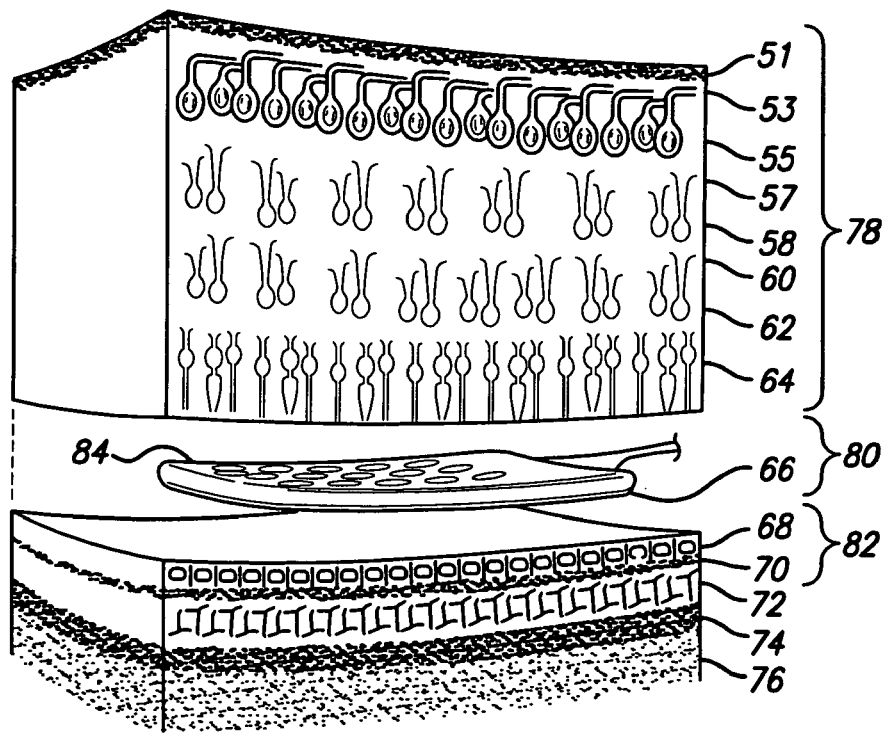
FIG. 6 illustrates a cross-sectional view of a retina showing the tissue layers and placement of the retinal implant in the retina for electrical stimulation of the retina.

A perspective cross-sectional view of the retina and outer wall of the eye is presented in FIG. 6. Moving from the inside of the eye outward, the structure of the eye is encountered as follows: internal limiting membrane 51, axons 53, ganglion and amacrine cell layer 55, inner plexiform 57, inner nuclear layer 58, outer plexiform layer 60, bipolar cell layer 62, photoreceptor cell layer 64, retinal pigment epithelium 68, Bruck's membrane 70, choriocapillaris 72, choroid 74, and the outer coat or sclera 76.

The inner retina 78 is generally the structures from the internal limiting membrane 50 to the photoreceptor cell layer 64. The outer retinal layer is the retinal pigment epithelium 68 and Bruck's membrane 70.

A subretinal implant position 80 is located between the photoreceptor cell layer 64 and the retinal pigment epithelium 68. In a preferred embodiment, the retinal implant 66 is surgically implanted in the subretinal implant position 80.

In a preferred embodiment, the retinal implant 66 is biocompatible and contains a number of arrayed electrodes 84, which are electrically stimulated by an outside source to stimulate the inner retinal layer 78, thereby to provide significantly useful formed vision. It is preferred that the electrodes 84 are located on the surface of the retinal implant 66 that faces the front of the eye, to stimulate the inner retinal layer 78.

Figure 7:
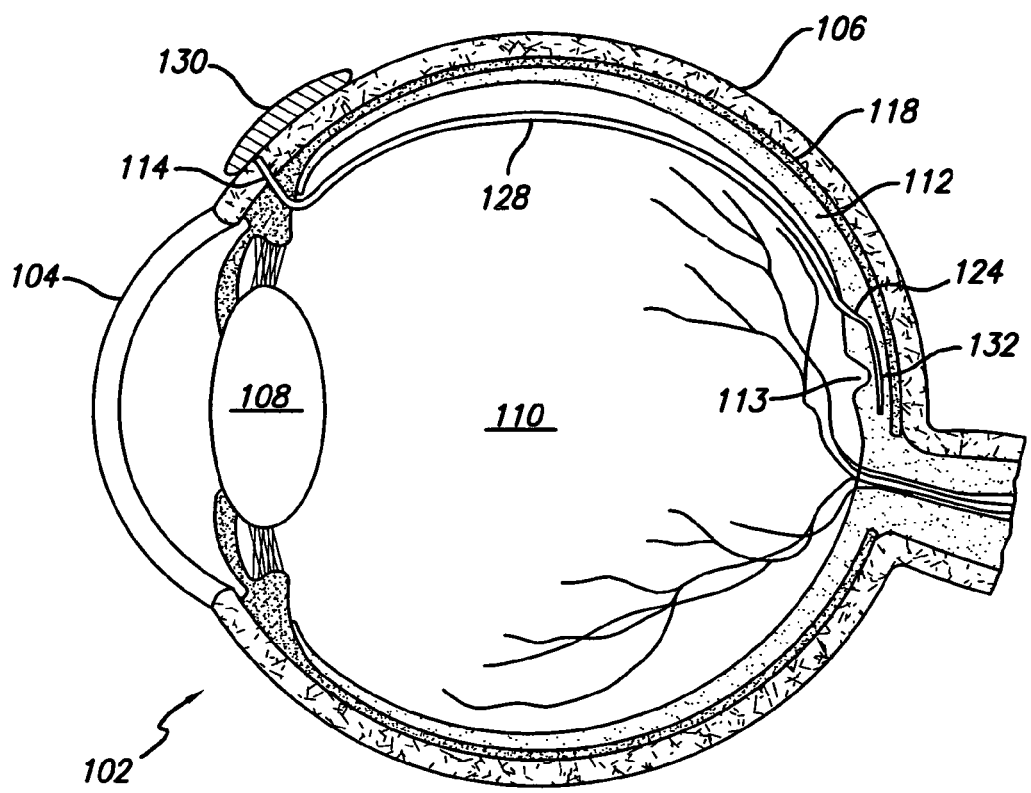
FIG. 7 illustrates a cross-sectional view of an eye showing placement of the retinal implant for drug delivery.

A cross-sectional view of the eye 102 and retinal implant 132 is presented in FIG. 7. In this embodiment of the invention, drugs are delivered by transfer from drug reservoir 130 to retinal implant 132, where the drugs are released subretinally for treatment of the tissue of the eye 2 and especially the retinal tissue. This device is particularly advantageous for treatment of chronic issues. A further advantage is that the quantity of drugs required and released to the eye is minimized by releasing the drugs in near proximity to the area of the eye 102 that requires treatment.

In a preferred embodiment, the drugs are transferred from drug reservoir 130 via delivery conduit 128, which is preferably a tube, to retinal implant 132. While the drugs may be pumped or delivered by other known means, it is preferable that they be delivered electrophoretically.

The structure of the eye 2, as shown in FIG. 7, presents a cornea 104 at the front of the eye with a lens 108 behind. The sclera 106 is on the outside of the eye and the choroid 118 is inside the eye 2 between the retina 112 and sclera 106.

The retinal implant 132 is implanted subretinally, preferably near the back of the eye. It is shown near the fovea 113, in FIG. 7, but may be located at other subretinal locations, as desired. The drug delivery conduit 128 connects the retinal implant 132 with the drug reservoir 130. The conduit 128 passes transretinally through retinal incision 124 and enters the vitreous cavity 110. The conduit 128 then passes transsclera at sclera incision 114 that passes through the sclera at a location near the front of the eye where there is no retina 112, thereby avoiding damage to the nutrient rich choroid 118 and avoiding disruption of the blood supply to the retina 112.

Figure 8:
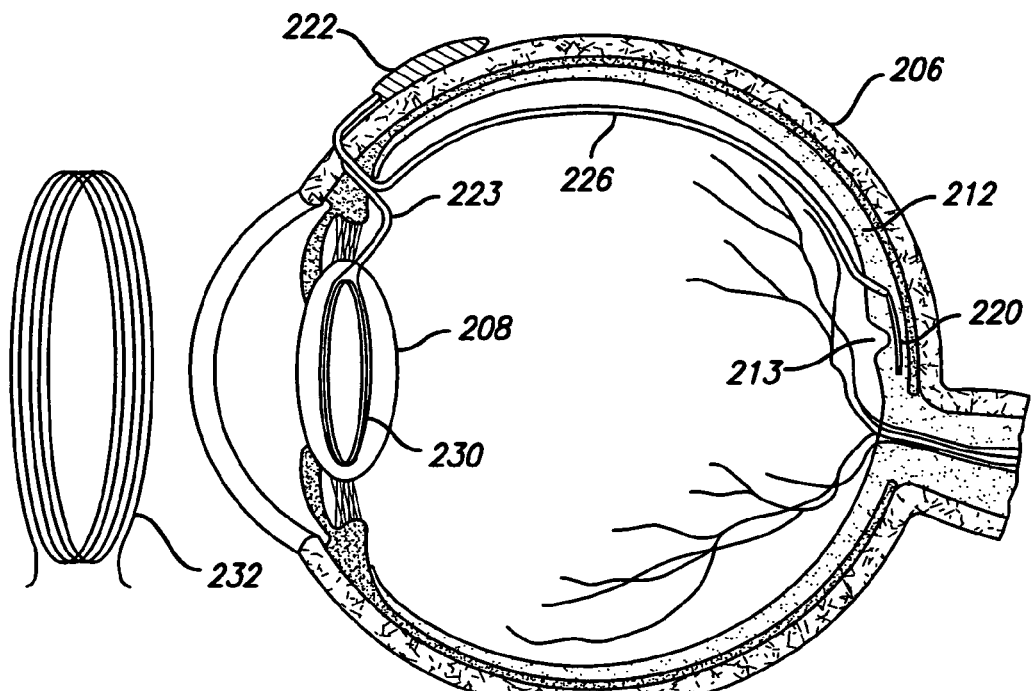
FIG. 8 illustrates a cross-sectional view of an eye showing the placement of the subretinal implant.

An alternative embodiment of a retinal implant to enable vision restoration is presented in FIG. 8, wherein a cross-section of the eye is presented showing the lens 208, retina 212, sclera 206, and fovea 213. U.S. Pat. No. 5,935,155, issued to Humayun, et al., the '155 patent, describes a similar visual prosthesis and method of use. In this embodiment, the retinal implant 220 is implanted subretinally. A primary coil 232 is located preferably either in an eyeglass lens frame or in a soft contact lens. This coil 232 is used to inductively couple the radio frequency encoded image signal to the secondary coil 230 that, in this embodiment, is implanted behind the iris of the eye. The control electronics 222 is placed in a hermetically sealed package and is coupled to a secondary coil 230 by a coil lead 223 that pierces the sclera 206 at a point near the lens 208 where there is no retina 212. The control electronics 222 is attached to the outside of the sclera 206. A lead wire 226 coupling the control electronics 222 to the retinal implant 220 passes transsclera at a point where there is no retina, preferably near the lens 208. The lead wire 226 passes inside the eye, preferably along the interior wall of the eye, and pierces the retina to pass transretinal to couple the control electronics 222 to the retinal implant 220. This invention is an improvement over that disclosed by the '155 patent because the retinal implant is subretinal rather than epiretinal, thereby facilitating stimulation of the retinal tissue.

Figure 9:
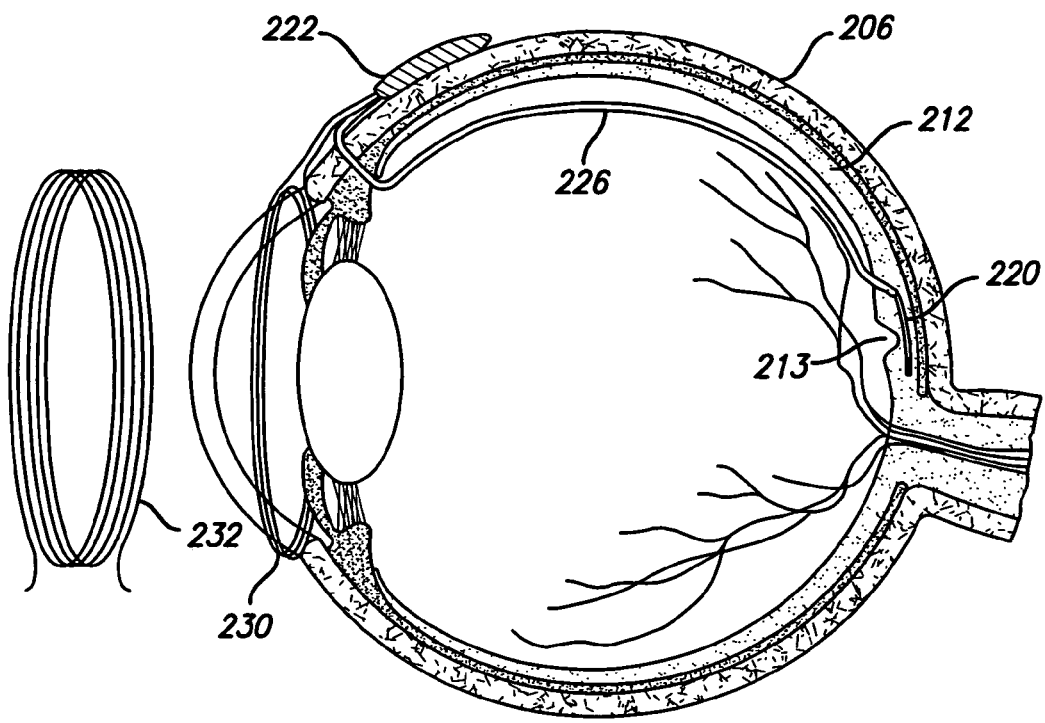
FIG. 9 illustrates a cross-sectional view of an eye showing the placement of the subretinal implant.

A further alternative embodiment of a retinal implant to enable vision restoration is presented in FIG. 9. The '155 patent discloses a similar invention, wherein the retinal implant 220 is placed subretinally. In this embodiment, the secondary 230 is attached to the sclera 206 instead of being implanted within the eye. As with the control electronics 222, the attachment of the secondary coil 230 to the sclera 206 may be by suturing or other appropriate means, as discussed in the '155 patent. In this way, only the lead wire 226 which attaches the control electronics 222 to the retinal implant 220 mounted subretinally below retina 212 is required to pierce the sclera 206. The extra-ocular attachment of the control electronics 222 allows increased access to this circuitry that eases the replacement or updating of these components.

Figure 10:
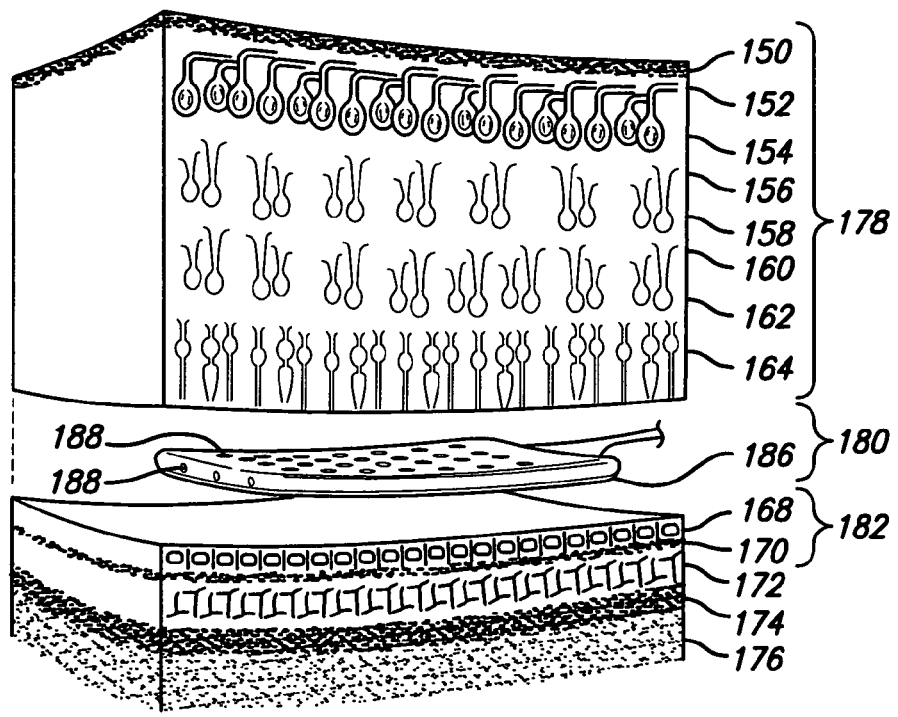
FIG. 10 illustrates a cross-sectional view of a retina showing the tissue layers and placement of the retinal implant in the retina for drug delivery

FIG. 10 presents a perspective cross-sectional view of the retina and outer wall of the eye. The tissue layers from the inside of the eye outward are the internal limiting membrane 150, axons 152, ganglion and amacrine cell layer 154, inner plexiform 156, inner nuclear layer 158, outer plexiform layer 160, bipolar cell layer 162, photoreceptor cell layer 164, retinal pigment epithelium 168, Bruck's membrane 170, choriocapillaris 172, choroid 174, and sclera 176.

The inner retinal layer 178 is comprised of tissue from the internal limiting membrane 150 to the photoreceptor cell layer 164. The outer retinal layer 182 consists of the retinal pigment epithelium 168 and Bruck's membrane 170.

Between the inner retinal layer 178 and outer retinal layer 182, is the subretinal implant position 180 in which retinal implant 186 is surgically located.

The retinal implant contains a number of orifices 188 through with the drug is released into the surrounding retinal tissue. The orifices 188 are preferably uniformly presented on both the inner and outer surfaces as well as on the edges of the retinal implant 186. However, the orifices 188 may be preferentially oriented in the retinal implant 186 to selectively release the drug on or near a desired tissue or location.

The invention relates to an implantable device to affect an eye, the eye having a retina, a sclera, and a vitreous cavity, said device comprising:
 a retinal implant that is positioned subretinally;
 said retinal implant comprising at least one electrode connected with a stimulating source;
 at least one connection with said stimulating source and with said at least one electrode, wherein said connection is suitable to pass transretinally into the vitreous cavity of the eye;
 said connection suitably designed to pass through the sclera at a point where there is no retina; and
 said stimulating source is suitable to be located outside the sclera.

The retinal implant is configured to enable electrical stimulation of a retina of an eye to produce artificial vision.

The stimulating source is comprised of a source of electrical signal. The connection is comprised of an electrical lead. At least one electrode that is configured to pass an electrical signal to the retina. The retinal implant that is positioned subretinally is suitable to be positioned between the photoreceptor cell layer and the retinal pigment epithelium. The stimulating source comprises electrical coupling with a secondary coil, which receives electromagnetic signals from a primary coil, said primary coil located outside the sclera. The secondary coil is suitable to be located inside the eye. The secondary coil is suitable to be located outside the sclera.

The invention relates to an implantable device to deliver drugs to an eye, the eye having a retina, a sclera, and a vitreous cavity, said device comprising:
 a retinal implant that is positioned subretinally for drug release;
 said retinal implant comprising a drug delivery device connected with a drug reservoir;
 at least one connection between said drug reservoir and said retinal implant, wherein said connection is suitable to pass transretinally into the vitreous cavity of the eye;
 said connection being suitable to pass through the sclera at a point where there is no retina; and
 said drug reservoir is located outside the eye.

The implantable device delivers the drugs electrophoretically. The connection comprises a tube. The retina additionally is comprised of a photoreceptor cell layer and a retinal pigment epithelium wherein said retinal implant that is positioned subretinally is suitable to be positioned between the photoreceptor cell layer and the retinal pigment epithelium.

The invention relates to an artificial retinal device to electrically stimulate a retina of an eye to produce artificial vision, the eye having a sclera, and a vitreous cavity, said artificial retinal device comprising:
 a retinal implant that is positioned subretinally;
 said retinal implant comprising at least one stimulating electrode connected with an electrical source that is located outside the eye;
 at least one electrical lead connected with said electrical source and with said at least one stimulating electrode, wherein said electrical lead is suitable to pass transretinally into the vitreous cavity of the eye; and
 said electrical lead passing through the sclera at a point where there is no retina.

The electrical source is suitable to affix to the sclera of the eye with sutures. The electrodes are facing the retinal. The retina additionally is comprised of a photoreceptor cell layer and a retinal pigment epithelium wherein said retinal implant that is positioned subretinally is suitable to be positioned between the photoreceptor cell layer and the retinal pigment epithelium.

The invention relates to an implantable device drug delivery device to deliver drugs for treatment to affect an eye, the eye having a retina, a sclera, and a vitreous cavity, said device comprising:
 a retinal implant that is positioned subretinally;
 said retinal implant comprising at least one orifice connected with a drug reservoir;
 at least one delivery conduit connected with said drug reservoir and with said at least one orifice, wherein said delivery conduit is suitable to pass transretinally into the vitreous cavity of the eye;
 said delivery conduit suitably designed to pass through the sclera at a point where there is no retina; and
 said drug reservoir is suitable to be located outside the sclera.

The implant releases said drugs electrophoretically. The delivery conduit is a tube that transfers said drugs from said drug reservoir to said retinal implant. The drug is suitable to stimulate living tissue. The retinal implant that is positioned subretinally is suitable to be positioned between the photoreceptor cell layer and the retinal pigment epithelium. The implantable device comprises an electrophoretic drug delivery device. The retinal implant is configured to enable drug stimulation of a retina of an eye to produce artificial vision.

The invention relates to a method for producing an artificial retinal device suitable to electrically stimulate a retina of an eye to produce artificial vision, the eye having a sclera, and a vitreous cavity, said method comprising the steps of:
 selecting a biocompatible retinal implant;
 placing at least one stimulating electrode in said retinal implant that is suitable for electrically stimulating the retina;
 connecting an electrical lead to said stimulating electrode;
 adapting said electrical lead to pass transretinally into the vitreous cavity of the eye;
 attaching said electrical lead to an electrical source that is located outside the eye; and
 passing said electrical lead through the sclera at a point where there is no retina.

The invention relates to a method for producing artificial vision in an eye using an artificial retinal device, the eye having a sclera, a retina, and a vitreous cavity, wherein said artificial retinal device comprises a retinal implant further comprising at least one stimulating electrode in said retinal implant, said stimulating electrode connected with an electrical source, at least one electrical lead connected with said electrical source and said electrode, the method comprising the steps of:
 adapting said retinal implant to be positionable in the subretinal position in the eye;
 adapting said electrical lead to be suitable to pass transretinally through the retina of the eye into the vitreous cavity; and
 adapting said electrical lead to be suitable to pass through the sclera at a point where there is no retina.

The method comprises the step of attaching said electrical source to the sclera by sutures.

The method further comprises the step of positioning said electrodes to face the retina.

The invention relates to a visual prosthesis, comprising:
 means for perceiving a visual image where said means is suitable to be located outside the eye of a user, said means producing a visual signal output in response thereto;

retinal tissue stimulation means adapted to be operatively attached to a retina of a user, where said retinal stimulation means is suitable to be located below the retina of a user; and wireless visual signal communication means for transmitting said visual signal output to said retinal tissue stimulation means.

The invention relates to a method of at least partially restoring vision to a user who suffers from photoreceptor degenerative retinal conditions of the eye, comprising the steps of:

perceiving a visual image and producing a visual signal output in response thereto;

wirelessly transmitting the visual signal output into the eye of a user; and stimulating retinal tissue of the user by means of an electrode, that is suitable to be placed below the retina of a user, in accordance with the visual signal output.

The invention relates to a flexible circuit electrode array comprising:

a polymer base layer;

metal traces deposited on said polymer base layer, including electrodes suitable to stimulate neural tissue; and said polymer base layer and said metal traces are embedded in a body having a generally oval shape in the plane of the retina, said oval shaped body being curved such that it substantially conforms to the spherical curvature of the retina of the recipient's eye.

The flexible circuit electrode array comprises at least one mounting aperture in said body for attaching the electrode array to the retina with a tack. The oval shaped body has a radius of spherical curvature, which is smaller than the radius of the curvature of the eye. The oval shaped body is made of a soft polymer containing silicone having hardness of about 50 or less on the Shore A scale as measured with a durometer. The flexible circuit cable portion has an angle of about 45° to about 180°. The flexible circuit cable portion has a bend with an angle of about 60° to about 120°. The flexible circuit cable portion has a bend with an angle of about 45° to about 180°. The flexible circuit cable portion has a bend with an angle of about 60° to about 120°. The flexible circuit cable portion has a fold within the attached flexible circuit electrode array with an angle of about 1° to about 180°. The flexible circuit cable portion has a fold within the attached flexible circuit electrode array with an angle of about 20° to about 90°. The flexible circuit cable portion has a horizontal angle within the attached flexible circuit electrode array of about 1° to about 90°. The flexible circuit cable portion has a horizontal angle within the attached flexible circuit electrode array of about 10° to about 45°. The flexible circuit cable portion comprises at least one grooved or rippled pad for capturing a mattress suture. The flexible circuit electrode array is positioned on the surface of the body having a generally oval shape. The soft insulating material is positioned on the surface between said electrodes. The film containing a soft polymer is applied on said flexible circuit cable portion. The film containing a soft polymer contains silicone. The film containing a soft polymer comprises a ladder like structure. The film containing a soft polymer contains beads and/or bumpers.

The invention relates to a method of making a flexible circuit electrode array comprising:

depositing a polymer base layer;

depositing metal on said polymer base layer;

patterning said metal to form metal traces;

depositing a polymer top layer on said polymer base layer and said metal traces; and heating said flexible circuit electrode array in a mold to form a three dimensional shape in said flexible circuit electrode array.

The method further comprising the steps of heating said flexible circuit electrode array in successively smaller molds. The step of depositing said polymer base layer and said polymer top layer is depositing polyimide. The step of depositing said polymer base layer and said polymer top layer is depositing silicone. The step of depositing said polymer base layer and said polymer top layer is depositing fluoro-polymer. The method further comprising forming a twist in a flexible circuit cable portion of said flexible circuit electrode array.

Obviously, many modifications and variations of the present invention are possible in light of the above teachings. It is therefore to be understood that, within the scope of the appended claims, the invention may be practiced otherwise than as specifically described.

Accordingly, what has been shown is an improved method making a neural electrode array and improved method of stimulating neural tissue. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A visual prosthesis adapted for subretinal stimulation, comprising:

a hermetic package including electrode drivers suitable to be implanted external to a sclera; and a flexible circuit attached to said hermetic package, the flexible circuit including:

a continuous polymer base layer including a cable region, an interconnection region and an electrode region, the electrode region pre-curved prior to implantation;

electrodes located in the electrode region, bond pads located in the interconnection region, and metal traces electrically connecting the electrodes in the electrode region with the bond pads in the interconnection region, the electrodes and the metal traces being on a concave side of said continuous polymer base layer, said electrodes in the electrode region forming an electrode array suitable to stimulate neural tissue, said bond pads in the interconnection region of the continuous polymer base layer adapted to electrically connect the flexible circuit to the hermetic package; and a continuous polymer top layer deposited on the cable region, the interconnection region and the electrode region of said concave side of said continuous polymer base layer, the continuous polymer top layer defining openings for said electrodes forming said flexible circuit electrode array;

wherein, when implanted, the cable region of the continuous polymer base layer is adapted to pass through a vitreous body and a pars plana.

2. The visual prosthesis according to claim 1, wherein said flexible circuit is pointed.

3. The visual prosthesis according to claim 1, wherein the bond pads are located within openings in the continuous polymer top layer on a same side of said flexible circuit as said openings for said electrodes.

4. The visual prosthesis according to claim 1, wherein said continuous polymer base layer, said metal traces and said continuous polymer top layer are curved to approximately a curvature of an eye.

5. The visual prosthesis according to claim 1, wherein said continuous polymer base layer, said metal traces and said continuous polymer top layer are thermoformed in a three dimensional shape.

6. The visual prosthesis according to claim 1, further comprising at least one bumper bonded to a peripheral edge of said flexible circuit.

7. The visual prosthesis according to claim 1, further comprising a narrowed portion in the cable region of said flexible circuit.

8. The visual prosthesis according to claim 1, wherein said continuous polymer top layer is a more compliant polymer than said continuous polymer base layer.

9. The visual prosthesis according to claim 1, further comprising a stress relief membrane suitable for attachment of said flexible circuit, wherein said stress relief membrane is made of a more compliant material than said continuous polymer base layer.

10. The visual prosthesis according to claim 1, further comprising a diagonal fold in the cable region of said flexible circuit.

11. The visual prosthesis according to claim 10, where said diagonal fold is across a dog leg in said flexible circuit.

12. The visual prosthesis according to claim 1, wherein the cable region comprises a widened portion suitable to resist movement of said flexible circuit.

13. The visual prosthesis according to claim 1, further comprising a secondary inductive coil electrically coupled with the hermetic package, the secondary inductive coil molded together with the hermetic package as a molded body.

14. The visual prosthesis according to claim 1, wherein the bond pads are on a side opposite the flexible circuit electrode array on the continuous polymer base layer.

* * * * *